US009017315B2

(12) United States Patent
Rathjen

(10) Patent No.: US 9,017,315 B2
(45) Date of Patent: *Apr. 28, 2015

(54) DEVICE FOR PROCESSING EYE TISSUE BY MEANS OF FEMTOSECOND LASER PULSES

(75) Inventor: Christian Rathjen, Bremen (DE)

(73) Assignee: SIE AG, Surgical Instrument Engineering (CH)

( * ) Notice: Subject to any disclaimer, the term of this patent is extended or adjusted under 35 U.S.C. 154(b) by 929 days.

This patent is subject to a terminal disclaimer.

(21) Appl. No.: 13/191,770

(22) Filed: Jul. 27, 2011

(65) Prior Publication Data

US 2012/0029492 A1 Feb. 2, 2012

Related U.S. Application Data

(60) Provisional application No. 61/368,731, filed on Jul. 29, 2010.

(51) Int. Cl.
*A61F 9/011* (2006.01)
*A61F 9/008* (2006.01)

(52) U.S. Cl.
CPC ......... *A61F 9/00827* (2013.01); *A61F 9/00836* (2013.01); *A61F 2009/00872* (2013.01); *A61F 2009/00897* (2013.01)

(58) Field of Classification Search
CPC .......... A61F 9/008; A61F 2009/00872; G02B 26/10; G02B 5/09
USPC .............................. 606/4, 5; 359/201.1–203.1
See application file for complete search history.

(56) References Cited

U.S. PATENT DOCUMENTS

| 4,725,709 A | 2/1988 | Mattelin ........................ 219/121 |
| 2004/0254568 A1 | 12/2004 | Rathjen ............................. 606/4 |
| 2006/0255243 A1 | 11/2006 | Kobayashi et al. ........ 250/208.1 |
| 2007/0010804 A1 | 1/2007 | Rathjen et al. .................... 606/5 |
| 2008/0049285 A1 | 2/2008 | Pinard et al. |
| 2008/0077121 A1 | 3/2008 | Rathjen ............................. 606/5 |
| 2008/0297869 A1 | 12/2008 | Akiyama et al. .............. 359/199 |

FOREIGN PATENT DOCUMENTS

| EP | 0176872 | 4/1986 |
| EP | 1486185 | 12/2004 |

(Continued)

*Primary Examiner* — William Thomson
*Assistant Examiner* — Jeffrey Lipitz
(74) *Attorney, Agent, or Firm* — Ostrolenk Faber LLP

(57) ABSTRACT

For processing eye tissue (8) by means of femtosecond laser pulses, an ophthalmological device (1) includes a projection optical unit (2) for the focused projection of the femtosecond laser pulses into the eye tissue (8). Disposed upstream of the projection optical unit (2) is a first beam-deflecting scanner system (3) for scanning the eye tissue (8) with the femtosecond laser pulses along a processing line (s). A second beam-deflecting scanner system (5) is disposed upstream of the first scanner system (3) and is designed for scanning the eye tissue (8) with the femtosecond laser pulses on a scanning curve (f) superimposed on the processing line (s). The second scanner system (5) has a scanner speed that is a multiple of the scanning speed of the first scanner system (3), and comprises at least one deflection mirror, a first scanning axis (51) and a second scanning axis (52). A control module (8) controls the deflection of the femtosecond laser pulses about the first scanning axis (51) and the deflection of the femtosecond laser pulses about the second scanning axis (52) in accordance with a defined curve shape, a defined curve amplitude and a defined curve orientation of the scanning curve (f).

16 Claims, 5 Drawing Sheets

(56) References Cited

FOREIGN PATENT DOCUMENTS

| | | |
|---|---|---|
| EP | 1731120 | 12/2006 |
| EP | 1897520 | 3/2008 |
| JP | 61-78587 | 4/1986 |
| JP | 5-173085 | 7/1993 |
| JP | 2006-317681 | 11/2006 |
| JP | 2006-341103 | 12/2006 |
| JP | 2008-299297 | 12/2008 |

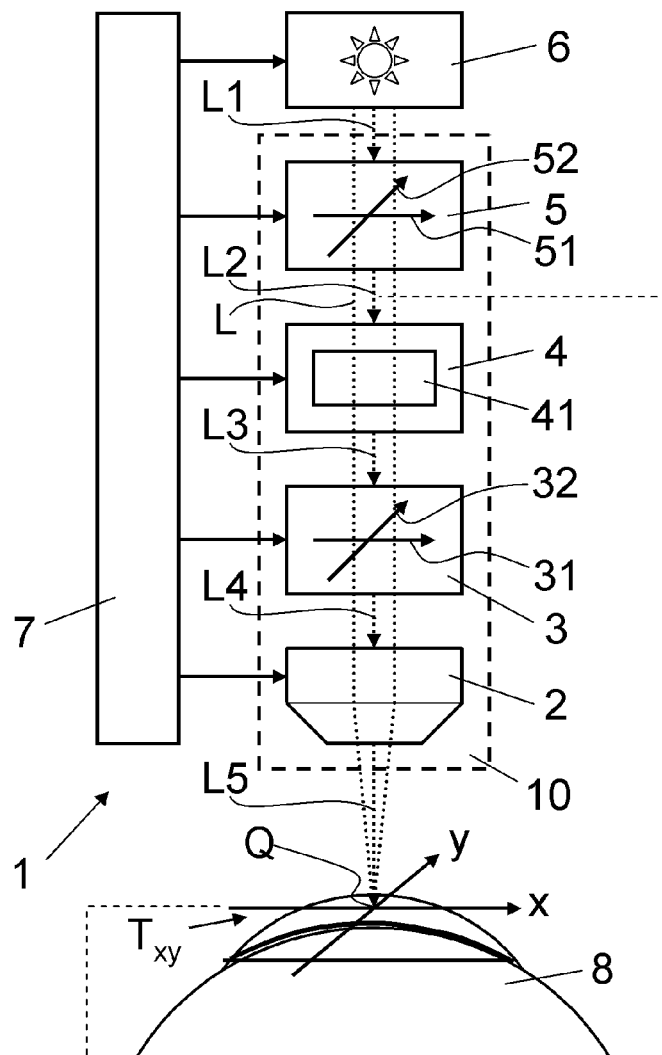
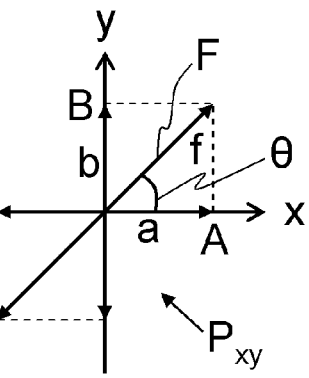
Fig. 1a
Fig. 1
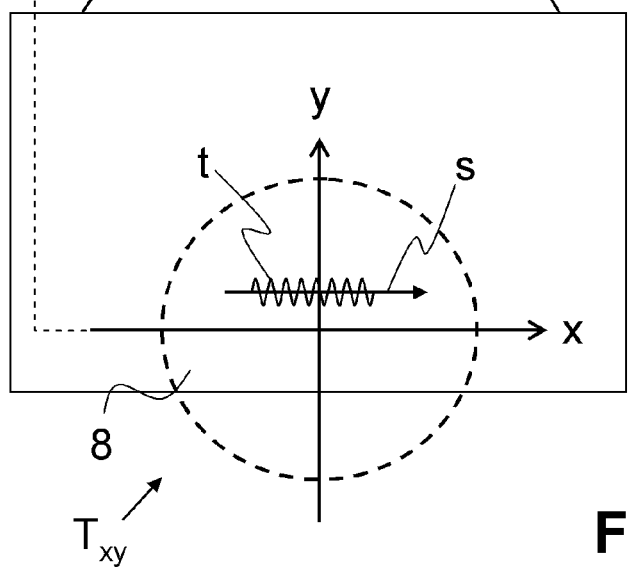
Fig. 1b

DEVICE FOR PROCESSING EYE TISSUE BY MEANS OF FEMTOSECOND LASER PULSES

CROSS REFERENCE TO RELATED APPLICATIONS

The present application claims benefit of and priority to U.S. Provisional Patent Application Ser. No. 61/368,731 filed Jul. 29, 2010 entitled VORRICHTUNG ZUM BEARBEITEN VON AUGENGEWEBE MITTELS FEMTOSEKUNDENLASERPULSEN, the entire contents of which are hereby incorporated by reference herein.

BACKGROUND

1. Field of the Disclosure

The present invention relates to an ophthalmological device for processing eye tissue by means of femtosecond laser pulses. The present invention relates, in particular, to an ophthalmological device including a projection optical unit for the focused projection of the femtosecond laser pulses into the eye tissue.

2. Related Art

For processing eye tissue by means of laser beams, an image region or a working region is scanned with laser pulses by means of the pulsed laser beam being deflected in one or two scanning directions by means of suitable scanner systems (deflection devices). The deflection of the light beams or of the laser pulses, for example femtosecond laser pulses, is generally performed by means of movable mirrors which are pivotable about one or two scanning axes, for example by means of galvanoscanners, piezoscanners or polygon scanners.

U.S. Pat. No. 7,621,637 describes a device for processing eye tissue, said device having a base station with a laser source for generating laser pulses and a scanner arranged in the base station with movable deflection mirrors for deflecting the laser pulses in a scanning direction. The deflected laser pulses are transmitted via an optical transmission system from the base station to an application head, which moves over a working region in accordance with a scanning pattern by means of a mechanically moved light projector. The deflection in the scanning direction, which is much faster compared with the mechanical movement, is superimposed in the application head onto the mechanical movement of the light projection and thus onto the scanning pattern thereof. A fast scanner system in the base station enables a fine movement of the laser pulses (microscan), which is superimposed onto the scanning pattern of the movable light projector that covers a large working region, for example the entire eye.

With the availability of faster laser pulses that yield ever higher pulse rates, for example more than one million pulses per second (MHz), the known scanner systems encounter their physical limits of being able to position pulses separately, and the pulse rate of the lasers has to be artificially reduced. In particular the mechanical movement of light projectors or lenses for scanning working regions, and also the mass inertia of galvanometer scanner systems, which does not permit arbitrarily high accelerations, limit the possible scanning patterns and scanning trajectories to the effect that greater changes in direction have to be avoided, and that the pulse rate has to be actively reduced (in a complicated manner) or the laser has to be switched off when the minimum scanning speed is undershot, for example at reversal points. Consequently, the known scanner systems impose significant limits on cut guidances that can be implemented. From a clinical standpoint, however, it is desired to plan the cut profile according to the biomechanical behaviour of the tissue, and not necessarily according to the speed and bandwidth of the scanner system, as is carried out with the known scanner systems. In contrast to surface processing, when cutting soft tissue, for example eye tissue, it is not always possible to employ simple pulse scanning patterns, for example line or spiral patterns, since tissue deformations can be caused by internal evolution of gas or release of stresses, and it is necessary to avoid said tissue deformations by means of suitably more complex scanning patterns taking account of the expected biomechanical behaviour of the tissue. Although the known scanner systems make it possible to process simple scanning patterns, for example to cut a tissue flap, this generally being performed as a large area segment with a simple edge geometry, in the case of isolated processing regions with a complicated edge geometry, such as are required for refractive correction, for example, or in the case of other, biomechanically governed more complex scanning patterns, that is no longer possible in such a simple manner. By way of example, it is then necessary for a large-area scanning pattern to be covered with a mask (electronically or optically), or the small regions are processed, e.g. scanned, individually, which results in a corresponding reduction of the processing speed, since the scanner system has to decelerate and accelerate very frequently relative to the section to be scanned.

SUMMARY

It is an object of the present invention to propose an ophthalmological device for processing eye tissue by means of femtosecond laser pulses which does not have at least some disadvantages of the known systems. In particular, it is an object of the present invention to propose an ophthalmological device for processing eye tissue by means of femtosecond laser pulses which manages without mechanical movement of lenses for the scanning of a processing region and allows the use of laser sources having high pulse frequencies, in particular pulse frequencies in the MHz range with more than one million pulses per second in order to reduce the processing time, and a more flexible cut guidance.

In accordance with the present invention, these aims are achieved by means of the features of the independent claims. Further advantageous embodiments additionally emerge from the dependent claims and the description.

The aims mentioned above are achieved by the present invention in particular by virtue of the fact that an ophthalmological device for processing eye tissue, in particular over the entire eye, by means of femtosecond laser pulses, which includes a projection optical unit for the focused projection of the femtosecond laser pulses into the eye tissue, is additionally provided with a first beam-deflecting scanner system disposed upstream of the projection optical unit, for scanning the eye tissue with the femtosecond laser pulses along a processing line, a second beam-deflecting scanner system disposed upstream of the first scanner system, for scanning the eye tissue with the femtosecond laser pulses on a scanning curve superimposed on the processing line, with a scanning speed that is a multiple of the scanning speed of the first scanner system, including at least one deflection mirror and a first scanning axis and a second scanning axis, and a control module for controlling the deflection of the femtosecond laser pulses about the first scanning axis and the deflection of the femtosecond laser pulses about the second scanning axis in accordance with a defined curve shape, a defined curve amplitude and/or a defined curve orientation of the scanning curve.

In the case of mirror-based scanner systems, the term scanning axis should be understood as equivalent to the mirror axis, such that a deflection of the mirror about the scanning axis brings about a deflection of a laser beam in a scanning direction running in the deflection plane. In the case of other scanner systems not having a mirror axis, the term scanning axis should be understood as a virtual axis about which a mirror would have to be rotated in order to deflect the laser beam in the relevant scanning direction.

For practical apparatus reasons and for cost reasons it is necessary to limit the size (e.g. the diameter) of the projection and transmission optical units in such a way that, in general, excursion or scanning angles of significantly less than 90 degrees can expediently be realized. In the case of a very small focus of the laser pulses (spots) such as are required for tissue-protective and precise processing, for example spots having a diameter of less than 5 µm, in particular less than 3 µm, preferably less than 1 µm, and a large image field (processing region), therefore, large beam diameters have to be scanned, which necessitates large and heavy mirrors and thus, as in the case of solutions with mechanically moved lenses, low scanning frequencies. In other words: for fundamental physical reasons, large image fields cannot be scanned with small (i.e. rapidly deflectable) mirrors and at the same time have spot diameters that are desirably small for the processing quality.

The cascading of the two beam-deflecting scanner systems with movable deflection mirrors enables eye tissue to be processed in a flexibly configurable and controllable manner, wherein the first scanner system covers an extended processing region, for example the entire eye, and the second scanner system disposed upstream superimposes a fast fine scanning movement, the form, size and orientation of which are flexibly adjustable, without overly large projection and transmission optical units having to be used, and without a mechanical movement of lenses or projection objectives being required for scanning, with the result that high scanning frequencies or scanning rates can be realized. The arrangement of the comparatively faster second scanner system, the "ultrafast scanner system", between the laser source and the first scanner system, the "fast main scanner system", allows the use of smaller beam apertures, e.g. mirrors, and thus enables fast, high-frequency scanning of the eye tissue. In this case, the faster second scanner system can be optimized for high-frequency scanning and processing, i.e. cutting, of the eye tissue with a relatively small excursion, and the first scanner system can be optimized for rapidly moving to any addressable points in the extended processing region (image region).

In one embodiment variant, the control module is designed to determine the curve orientation of the scanning curve by coupled control of the excursion amplitude of the deflection about the first mirror axis and of the excursion amplitude of the deflection about the second mirror axis. As a result of the simple control of the curve orientation on the basis of the excursion amplitudes, a costly and slow mechanical and/or optical image rotator becomes invalid, since the control is effected entirely by electronic and/or programming means.

In one embodiment variant, the control module is designed to determine the curve orientation of the scanning curve by coupled control of the excursion amplitude of the deflection about the first mirror axis, of the excursion amplitude of the deflection about the second mirror axis, and of the relative phase of the deflection about the first mirror axis and of the deflection about the second mirror axis. The coupled control of the excursion amplitudes and relative phase makes it possible, for example, to control the orientation of an ellipse.

In a further embodiment variant, the control module is designed to determine the curve amplitude of the scanning curve by coupled control of the excursion amplitude of the deflection about the first mirror axis and of the excursion amplitude of the deflection about the second mirror axis.

In one embodiment variant, the control module is designed to determine the curve shape of the scanning curve by control of the relative phase between the deflection about the first mirror axis and the deflection about the second mirror axis.

In a further embodiment variant, the control module is designed to determine the curve shape of the scanning curve by coupled control of the excursion amplitude of the deflection about the first mirror axis and of the excursion amplitude of the deflection about the second mirror axis.

In a further embodiment variant, the control module is designed to determine the curve shape of the scanning curve by coupled control of the deflection frequency about the first mirror axis and of the deflection frequency about the second mirror axis.

In one embodiment variant, the control module is designed to determine a curve shape—definable by Fourier synthesis—of the scanning curve by control of the excursion amplitude of the deflection about the first mirror axis, the excursion amplitude of the deflection about the second mirror axis, the relative phase between the deflection about the first mirror axis and the deflection about the second mirror axis, the deflection frequency about the first mirror axis, and/or the deflection frequency about the second mirror axis.

Preferably, the control module is designed to control the first scanner system and the second scanner system in coupled fashion.

Preferably, the control module is designed to control, depending on the processing line, the excursion amplitude of the deflection about the first mirror axis, the excursion amplitude of the deflection about the second mirror axis, the relative phase between the deflection about the first mirror axis and the deflection about the second mirror axis, the deflection frequency about the first mirror axis and/or the deflection frequency about the second mirror axis.

In one embodiment variant, the control module is designed, in the case of a change in the direction of the processing line, to increase the excursion amplitude of the deflection about the first mirror axis and to reduce the excursion amplitude of the deflection about the second mirror axis. The excursion amplitudes are reduced and respectively increased continuously, for example.

In a further embodiment variant, the control module is designed to control the deflection about the first mirror axis and the deflection about the second mirror axis such that the deflection about the first mirror axis is effected with a deflection frequency having a doubled magnitude relative to the deflection about the second mirror axis, and the deflection about the first mirror axis brings about at least partial compensation of the deflection brought about by the first scanner system in the direction of the processing line.

In a further embodiment variant, the device includes a diaphragm arranged between the first scanner system and the second scanner system and serving for masking out femtosecond laser pulses that are deflected by the second scanner system into a region outside a defined scanning width.

In a further embodiment variant, the device includes a controllable filter module for selectively excluding femtosecond laser pulses in a defined region of the scanning curve.

Preferably, the first mirror axis and the second mirror axis of the second scanner system are oriented orthogonally with respect to one another, the second scanner system is designed to deflect the femtosecond laser pulses in an oscillating fashion about the first mirror axis and about the second mirror axis, and the first scanner system has a significantly greater degree of excursion in comparison with the second scanner system.

In one embodiment variant, the control module is designed to control the deflection of the femtosecond laser pulses about the first mirror axis and the deflection of the femtosecond laser pulses about the second mirror axis such that the scanning curve has a round curve shape, and the control module is designed to control the scanning speed of the first scanner system such that a resulting scanning trajectory having a defined trajectory profile arises from the superimposition of the scanning curve onto the processing line. When a circular scanning curve is superimposed onto the processing line, control of the scanning curve with regard to its orientation becomes dispensable on account of the symmetry.

BRIEF DESCRIPTION OF THE DRAWINGS

An embodiment of the present invention is described below on the basis of an example. The example of the embodiment is illustrated by the following enclosed figures:

FIG. 1: shows a block diagram schematically illustrating an ophthalmological device including two cascaded scanner systems for processing eye tissue by means of femtosecond laser pulses.

FIG. 1a: schematically shows a projection plane of one of the scanner systems with two scanning axes oriented orthogonally with respect to one another.

FIG. 1b: schematically shows a processing plane with a scanning trajectory resulting from the cascading of the scanner systems.

FIG. 8b: illustrates the superimposition of the round scanning curve onto the round processing line, wherein the scanning curve has an opposite sense of rotation with respect to the scanning curve from FIG. 8a.

DETAILED DESCRIPTION OF THE EMBODIMENTS

Figure 2:
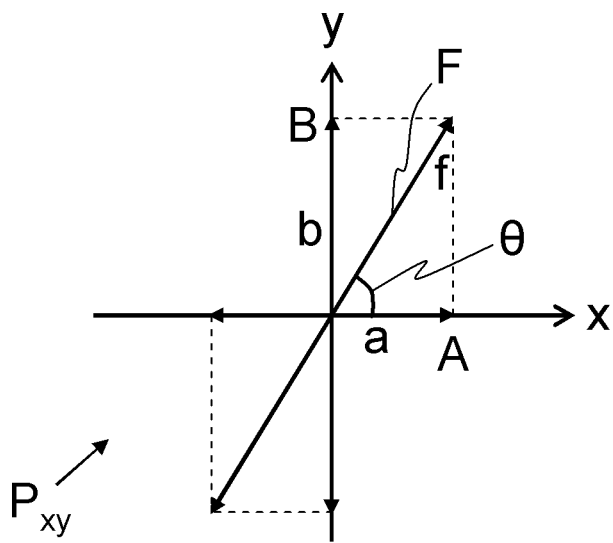
FIG. 2: illustrates the superimposition of scanning movements about two mirror or scanning axes arranged orthogonally with respect to one another, said scanning movements oscillating in a manner that is not phase shifted.

In FIG. 1, the reference symbol 1 refers to an ophthalmological device for processing eye tissue 8 by means of a pulsed laser beam L1 with femtosecond laser pulses. The pulsed laser beam L1, preferably having pulse frequencies in the MHz range with more than one million pulses per second, is supplied by a beam source 6 and, in a manner focused by means of an optical transmission system 10, projected along a scanning trajectory t as a pulsed processing beam L5 onto or into the eye tissue 8. Depending on the embodiment, the beam source 6 is part of the optical transmission system 10 or configured as a separate unit connected to the optical transmission system 10 via a light transmission system, for example a fibre-optic line and/or a mirror/lens system.

As is illustrated schematically in FIG. 1, the ophthalmological device 1 or the optical transmission system 10 includes two beam-deflecting scanner systems 3, 5 and an optional filter module 4, which are arranged in the beam path (l1-L2-L3-L4) from the beam source 6 to the projection optical unit 2.

The beam-deflecting scanner system 5 has a scanning speed that is a multiple of the scanning speed of the scanner system 3 Accordingly, in the following description, the scanner system 5 is designated as fast scanner system 5 and the scanner system 3 as slow scanner system 3. Consequently, the fast scanner system 5 has a deflection speed that is faster by a multiple, and, in the case of oscillating scanner systems, oscillation frequencies ($\omega_x$, $\omega_y$) that are higher by a multiple relative to what would be feasible with the slow scanner system 3. In particular, the fast scanner system 5 has a higher scanning speed in the image field of the projection objective (cutting objective), that is to say in the image field of the projection optical unit 2, and/or has a higher scanning frequency. On the other hand, the slow scanner system 3 has a significantly greater degree of excursion in the image field of the projection optical unit in comparison with the fast scanner system 5. Consequently, the slow scanner system 3 makes it possible to cover and address a much larger image field and processing region in comparison with the fast scanner system 5, such that the eye tissue 8 can be scanned completely over the entire eye and be processed with femtosecond laser pulses.

The fast scanner system 5 is preferably arranged between the beam source 6 and the slow scanner system 3. The fast scanner system 5 is arranged for example in the beam path directly downstream of the beam source 6.

The slow scanner system 3 is preferably arranged between the fast scanner system 5 and the projection optical unit 2. The slow scanner system 3 is arranged for example in the beam path directly upstream of the projection optical unit 2.

The fast scanner system 5 has two mirror axes 51, 52, which are preferably oriented orthogonally with respect to one another. Depending on the embodiment variant, the scanning axes (mirror axes) 51, 52 are coupled to a common, tiltable (tip-tilt mode) deflection mirror or to a respective dedicated, separate deflection mirror, which are arranged in a cascaded fashion. The use of a scanner system having two scanning axes 51, 52 and a common tiltable deflection mirror has the advantage that costly intermediate optical units can be saved and the entire construction of the device 1 turns out to be more compact. The fast scanner system 5 deflects the pulsed laser beam L1 from the beam source 6 or the femtosecond laser pulses thereof with a defined scanning movement onto a scanning curve f, defined in a projection plane $P_{xy}$, as will be described in detail later with reference to FIGS. 2, 3 and 4. FIG. 1a schematically illustrates a projection plane $P_{xy}$ of the fast scanner system 5, wherein the scanning axis 51 is oriented along the x-axis and the scanning axis 52 is oriented along the y-axis. The movement vector a represents the excursion of the deflection mirror about the scanning axis 52 (y-axis) with an excursion amplitude A in the x-direction, and the movement vector b represents the excursion of the deflection mirror about the scanning axis 51 (x-axis) with an excursion amplitude B in the y-direction. In the case of a synchronized excursion, i.e. one that is at the same frequency ($\omega_x = \omega_y$) and not phase shifted ($\phi = 0$), about the two scanning axes 51, 52, the femtosecond laser pulses are deflected along a scanning curve f, which is represented by a corresponding movement vector in FIG. 1a. The excursion amplitudes A, B thus determine the orientation θ and excursion amplitude F of the resulting scanning movement or scanning curve f of the scanner system 5 on the projection plane $P_{xy}$.

The slow scanner system 3 preferably likewise has two scanning axes (mirror axes) which are oriented orthogonally with respect to one another and which are coupled to a common, tiltable deflection mirror or to two separate deflection mirrors.

Preferably, the slow scanner system 3 is embodied as freely addressable in the form of two galvanometer scanners or with a two-axis deflection mirror that is tiltable in the tip-tilt mode (e.g. governed by means of piezoelements). Depending on the operating mode or construction, the fast scanner system 5 is embodied as a resonant, oscillating, or freely addressable scanner. A sinusoidal operating mode allows, particularly in the case of mechanical resonance scanners with oscillating mirrors (also referred to as MEM (micro electromechanical) scanner or with a piezo-drive), higher frequencies and deflection speeds than are possible with galvanometer scanners. Therefore, use is preferably made of oscillating fast scanner systems 5 in the resonant operating mode, since they are particularly advantageous for practical use on account of their high scanning frequencies. Further scanner types, which in some instances allow even higher frequencies, are known from the literature (e.g. AOM (acousto-optical modulators) scanners or EOM (electro-optical modulators)). Preferably, the fast scanner system 5 and the slow scanner system 3 are embodied and operated with orthogonal scanning axes (mirror axes).

The optional filter module 4 is arranged in the beam path preferably between the fast scanner system 5 and the slow scanner system 3. Depending on the embodiment variant, the filter module 4 includes a fixed and/or controllable diaphragm 41, which can also be embodied as a shutter, wherein the shutter is preferably arranged at the laser and disposed directly downstream of the beam source 6. In one embodiment variant, the diaphragm 41 is embodied as a field stop, that is to say arranged in an intermediate image plane, wherein, moreover, depending of the embodiment variant, the field stop is configured as variable and/or asymmetrical.

The slow scanner system 3 is designed to scan the eye tissue 8 with the femtosecond laser pulses in an extended processing region along a processing line s. In this case, the slow scanner system 3 deflects the femtosecond laser pulses L2 deflected by the fast scanner system 5 or the femtosecond laser pulses L3 filtered and not masked out by the filter module 4. The direction and shape of the processing line s are determined, as described above with reference to FIG. 1a for the fast scanner system 5, by the excursion amplitudes of the excursions about the scanner axes (mirror axes) 31, 32 of the slow scanner system 3. The scanning movement or scanning curve f produced by the fast scanner system 5 is therefore superimposed on the processing line s continuously scanned by the slow scanner system 3, whereby a resulting scanning trajectory t is formed in the processing plane $T_{xy}$, as illustrated in FIG. 1b, with which trajectory the eye tissue 8 is actually processed. FIGS. 5, 6, 7, 8a and 8b illustrate examples of different scanning trajectories t produced for processing the eye tissue 8 on a processing plane $T_{xy}$, which will be discussed in detail later.

The filter module 4 is designed to mask out certain ones of the femtosecond laser pulses L2 deflected by the fast scanner system 5, in accordance with defined filter criteria. The diaphragm 41 is designed for example in fixed or controllable fashion to mask out femtosecond laser pulses L2 deflected by the fast scanner system 5 into a region outside a defined scanning width E, or to exclude deflected femtosecond laser pulses L2 completely or in a defined region R1, R2 of the scanning curve f. In the example in FIG. 5, the filter module 4 is designed to mask out the peaks of the excursions b, for example above a defined amplitude value B, in the region R1. In the example in FIG. 6, the filter module 4 is designed to mask out in each case the rising edges of the scanning trajectory t in the region R2, such that a scanning pattern with virtually parallel scanning sections is produced. The masking-out regions R1, R2 are for example dynamically and freely definable and alterable, for example depending on the excursions a, b about the mirror axes 51, 52 and/or on the direction of the processing line s.

The projection optical unit 2 is designed to project the femtosecond laser pulses L4 deflected by the slow scanner system 3 in a focused fashion onto or in the eye tissue 8, wherein the eye tissue 8 is resolved at the focal point Q, depending on the scanning speed in the direction of the processing line s, in each case by an individual femtosecond laser pulse or by a plurality of femtosecond laser pulses projected successively in an overlapping fashion. In one embodiment variant, the projection optical unit 2 is additionally designed to set the focus Q of the focussed, deflected, pulsed laser beam L5, for example by vertical displacements, in the projection direction. Otherwise, the projection optical unit 2 is stationary during the treatment, that is to say that the scanning and processing of the eye tissue 8 does not require any lateral mechanical movement (in the x- and/or y-direction) of lenses of the projection optical unit 2 after the latter has been aligned with the patient's eye for the planned treatment. Fixing to the eye is effected, for example, by means of a vacuum-controlled suction ring.

As can be seen in FIG. 1, the ophthalmological device 1 includes a control module 7, which, depending on the embodiment, is configured as part of the optical transmission system 10 or as a separate unit connected to the optical transmission system 10 via control lines or one or a plurality of data communication connections, for example a plurality of signal and/or data lines and/or a data bus, for control purposes. Depending on the embodiment, the control module 7 is connected to the beam source 6, the fast scanner system 5, the filter module 4, the slow scanner system 3 and/or the projection optical unit 2. The control module 7 preferably includes one or a plurality of processors and an accessible computer-readable data carrier (computer program product), which is connected to the processors in a fixed or removable fashion and on which at least one programmed software module is stored which includes computer program code for controlling the processors. The person skilled in the art will understand that the control module 7 can be implemented in different embodiment variants completely or at least partly with hardware components.

The following sections describe the functionality of the control module 7 and the control brought about thereby of the processors and thus of the ophthalmological device 1 with reference to FIGS. 2, 3, 4, 5, 6, 7, 8a and 8b.

Depending on the embodiment variant, the control module 7 is designed to control the beam source 6 and/or the projection optical unit 2, for example with regard to pulse energy, pulse frequency or depth of focus, although this will not be described in greater detail in the following sections.

The control module 7 includes, in particular, a fast scanner controller for controlling the deflection a, b of the femtosecond laser pulses about the mirror axes 51, 52 of the fast scanner system 5. As is indicated in Table 1, the fast scanner controller is designed to control the deflection a, b about the mirror axes 51, 52 for implementing defined scanning curves f, which are defined by a different curve shape, curve orientation and curve amplitude (or curve size) and have, for example, an assigned unique curve identifier. In order to deflect the femtosecond laser pulses onto a selected defined scanning curve f, the control module 7 uses corresponding control parameters for controlling the fast scanner system 5 which are assigned to the relevant scanning curve f. The excursions about the mirror axes 51, 52 are determined, in particular, with parameters for controlling the respective excursion amplitudes A, B, excursion frequency $\omega_x$, $\omega_y$ and/or relative phase $\phi$ (phase shift) between the excursions a, b (oscillation) about the mirror axes 51, 52.

sions a, b about the scanning axes 51, 52 by means of the control module 7. The example shows the generation of a Lissajous-shaped resulting scanning curve f in the case of a setting of the excursion frequency $\omega_y$ of the excursion x in the x-direction about the scanning axis 52 (y-axis) by the control module 7 to double the value of the excursion frequency $\omega_x$ of the excursion b in the y-direction about the scanning axis 51 (x-axis), $\omega_y = 2\omega_x$.

The control module 7 or the fast scanner controller is designed to control the deflection a, b of the femtosecond laser pulses about the mirror axes 51, 52 with regard to their excursion amplitudes A, B, excursion frequencies $\omega_x$, $\omega_y$ and relative phase $\phi$ in such a way that, alongside classic Lissajous figures, resulting scanning curves f with sinusoidal, sawtooth-shaped, trapezium-shaped or rectangular oscillations or other shapes arise which can be produced by means of Fourier synthesis. In the case of freely drivable scanning axes 51, 52, non-periodic figures can additionally be produced as well.

The control module 7 additionally includes a slow scanner controller for controlling the deflection of the femtosecond laser pulses about the mirror axes 31, 32 of the slow scanner system 3. The slow scanner controller is designed, for example, to control the deflection about the mirror axes 31, 32 in accordance with defined processing lines s which are defined by different processing patterns and have, for example, an assigned unique pattern or line identifier. In order to deflect the femtosecond laser pulses onto a processing line s defined, for example, by a stored processing pattern or a time function, the control module 7 uses corresponding con-

TABLE 1

| | | | Control parameter | | | | | |
|---|---|---|---|---|---|---|---|---|
| | Scanning curve | | | Excursion about first scanning axis | | Excursion about second scanning axis | | Phase |
| Identifier | Shape | Orientation | Amplitude | Amplitude | Frequency | Amplitude | Frequency | shift |
| ... | ... | ... | ... | ... | ... | ... | ... | ... |

FIG. 2 illustrates an example of how, by the control of the excursion amplitudes A, B about the scanning axes 51, 52, the orientation θ and excursion amplitude F of the resulting scanning movement f on the projection plane $P_{xy}$ can be set by the control module 7 if the remaining control parameters are set in such a way that the deflection a, b about the two scanning axes 51, 52 is effected with the same frequency $\omega_x = \omega_y$ and without a phase shift $\phi = 0$ between the excursion oscillations.

Figure 3:
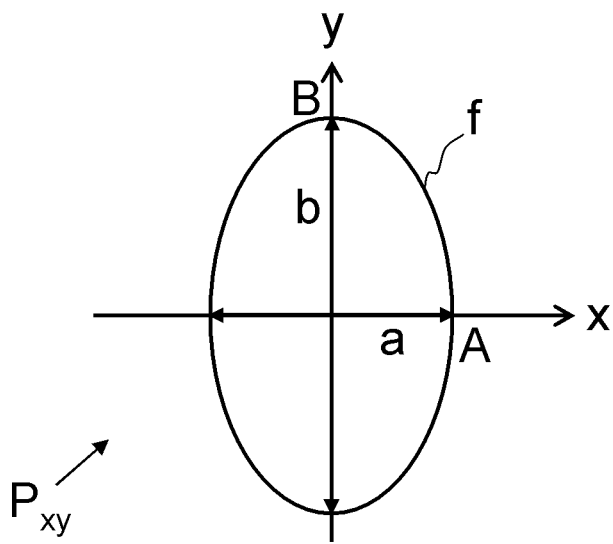
FIG. 3: illustrates the superimposition of scanning movements about two mirror or scanning axes arranged orthogonally with respect to one another, said scanning movements oscillating in a manner phase shifted by $\pi/2$.

FIG. 3 shows an example in which the relative phase $\phi$ between the sinusoidally oscillating excursions a, b about the scanning axes 51, 52 can additionally be set by means of a phase actuating element, for example a part of the control module 7. The example shows a driving of the fast scanner system 5 with a phase shift of $\phi = \pi/2$ between the excursions about the scanning axes 51, 52 with the same excursion amplitudes A, B as in the example in FIG. 2, such that a resulting scanning curve f having an elliptical shape is produced in the projection plane $P_{xy}$ by the fast scanner system 5. The orientation θ of the resulting ellipse can be set by simultaneously setting the excursion amplitudes A, B and the relative phase $\phi$. Given the same size of the excursion amplitudes A, B, a circular scanning curve f results.

Figure 4:
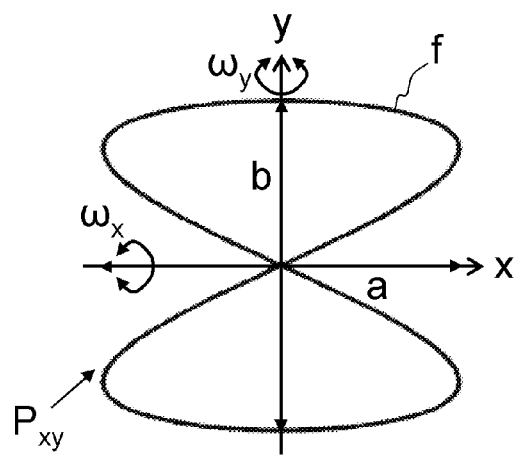
FIG. 4: illustrates the superimposition of scanning movements about two mirror or scanning axes arranged orthogonally with respect to one another, said scanning movements oscillating in a manner phase shifted by $\pi/2$ and with different frequencies.

FIG. 4 shows an example of how the shape of the resulting scanning curve f can furthermore be determined by setting and controlling the excursion frequencies $\omega_x$, $\omega_y$ of the excurtrol parameters for controlling the slow scanner system 3 which are assigned to the relevant processing line s.

In the control of the fast scanner system 5 and of the slow scanner system 3 by the control module 7, substantially three operating modes can be differentiated:

a) In fully coupled operation, both the excursion amplitudes A, B and the relative phase $\phi$ of the deflections a, b about the two scanning axes 51, 52 of the fast scanner system 5 are synchronized with the slow scanner system 3 (for example with a start point at $T_{xy}$ or an absolute phase value as reference point). This operating mode or the embodiment variant is chosen when both the orientation θ and the shape of the scanning curve f are intended to be controlled with respect to and depending on the processing line s, in particular depending on the direction and the scanning speed (advancing speed) of the processing line s, for example for the control of the phase angle for the specific and defined (intendable) positioning of successive laser pulses on the resulting scanning trajectory t.

b) In partly coupled operation, a subset of excursion amplitudes A, B, excursion frequencies $\omega_x$, $\omega_y$ and relative phase $\phi$ of the two scanning axes 51, 52 of the fast scanner system 5 is controlled or set depending on the processing line s of the slow scanner system 3. This operating mode or the embodiment variant is chosen when primarily the orientation θ and/or the size of the scanning curve f are/is intended to be controlled with respect to the processing line s for the purpose of producing a desired scanning trajectory t.

c) In decoupled operation, the orientation θ of the scanning curve f with respect to the processing line s is of no importance and the size (amplitude F) is fixedly predefined.

Figure 5:
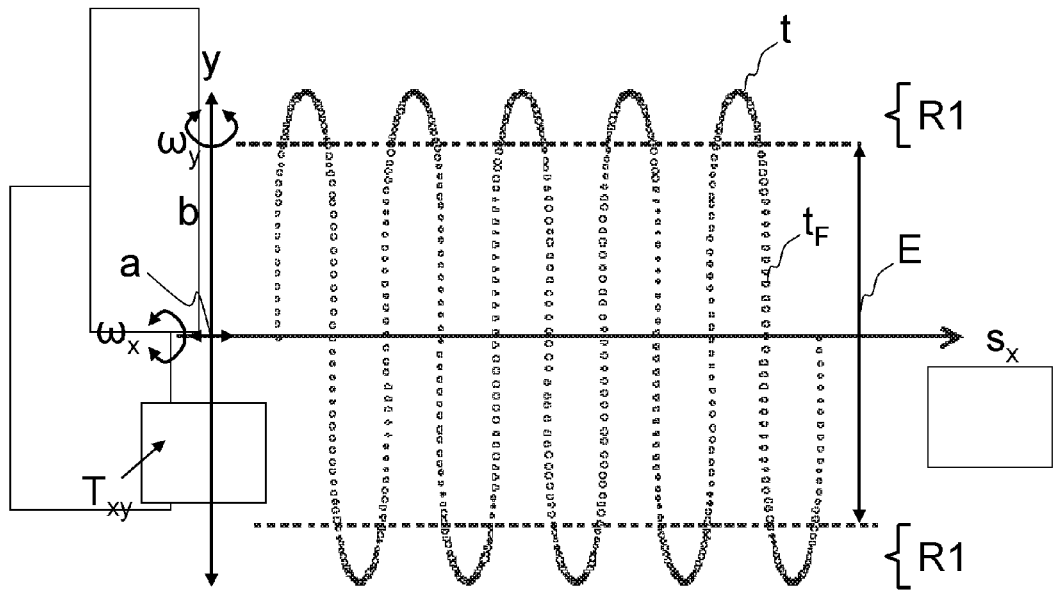
FIG. 5: illustrates the superimposition of a scanning curve of one scanner system having two mirror or scanning axes onto the processing line of a further scanner system, wherein, for edge straightening, the deflection about one of the mirror axes is effected with a deflection frequency having a doubled magnitude relative to the deflection about the other mirror axis.

FIG. 5 shows an example of how a scanning trajectory t having straightened edges $t_F$ of the oscillations—orthogonal with respect to the processing line $s_x$—of the excursion b about the scanning axis 51 is produced. As is illustrated schematically in FIG. 5, the control module 7 or a straightening module is designed to control the fast scanner system 5 in such a way that the excursion a in the x-direction about the scanning axis 52 is effected with a doubled excursion frequency $\omega_y = 2\omega_x$ of the excursion b in the y-direction about the scanning axis 51. In this case, the excursion amplitude A is set in a manner dependent on the excursion amplitude B and the scanning speed of the slow scanner system 3 in the direction of the processing line $s_x$ in such a way as to compensate for the movement components in the (x-)direction of the processing line $s_x$ at the rising and falling edges $t_F$ of the orthogonal excursion oscillations for the purpose of straightening the oscillation edges $t_F$ (the masking out of parts of the trajectory t can thus advantageously be dispensed with).

Figure 7:
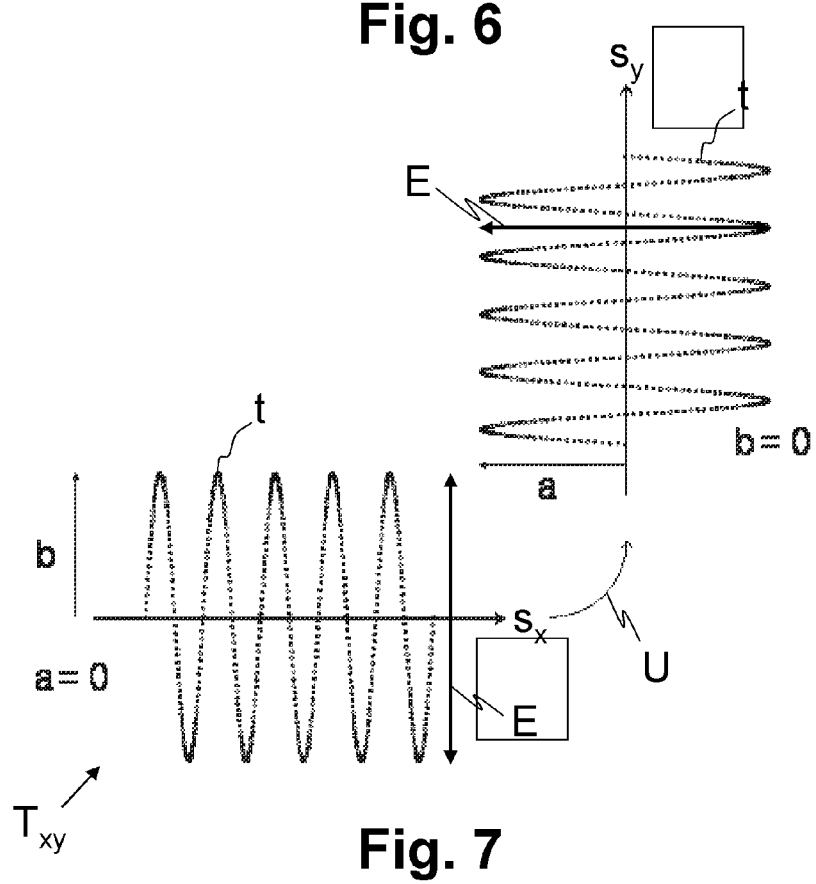
FIG. 7: illustrates the superimposition of a scanning curve of a scanner system having two mirror or scanning axes onto the processing line of a further scanner system wherein, for keeping to the scanning width and the orientation with respect to the processing line, in the case of a change in the direction of the processing line, the excursion amplitudes of the deflections about the mirror or scanning axes are adapted.

FIG. 7 shows an example of how a scanning trajectory t is adapted to a change in the direction of the processing line $s_x$, $s_y$, for example from the x-direction to the y-direction. As is illustrated schematically in FIG. 7, the control module 7 or a rotator module is designed to control the fast scanner system 5 in such a way that it sets the excursion amplitude B of the excursion b in the y-direction about the scanning axis 51 and the excursion amplitude A of the excursion a in the x-direction about the scanning axis 52 depending on the direction of the processing line $s_x$, $s_y$, for example in such a way that, during the processing by the slow scanner system 3 along the processing line $s_x$ in the x-direction, the excursion amplitude B of the fast scanner system 5 is set to a defined scanning width E and the excursion amplitude A of the fast scanner system 5 is set to zero, and, conversely, during the processing by the slow scanner system 3 along the processing line $s_y$ in the y-direction, the excursion amplitude A of the fast scanner system 5 is set to the defined scanning width E and the excursion amplitude B is set to zero. In the transition region U from processing in the x-direction to processing in the y-direction, the excursion amplitudes A, B of the fast scanner system 5 are continuously increased and reduced, respectively, for example.

Figure 6:
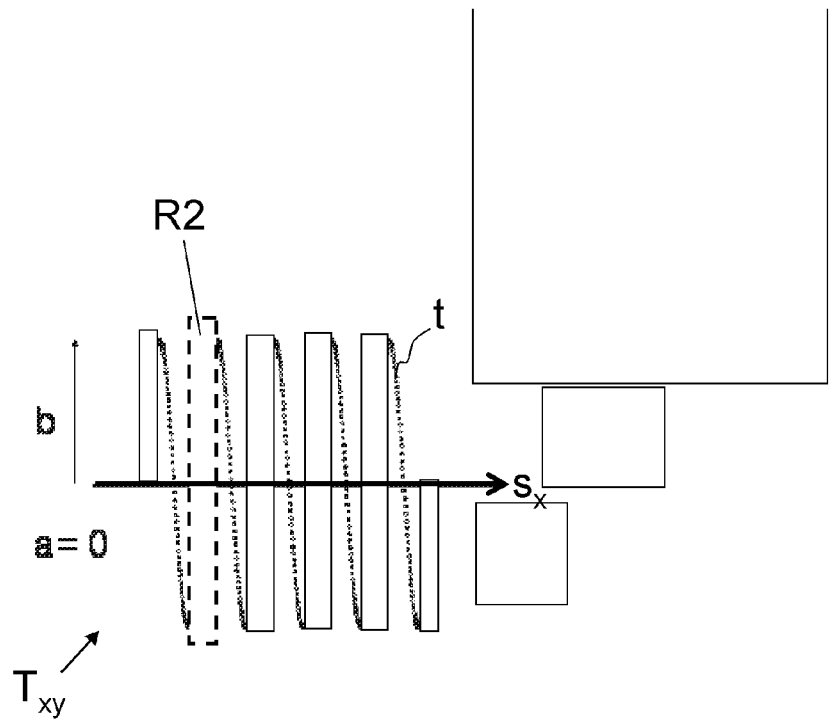
FIG. 6: illustrates the superimposition of a scanning curve of one scanner system having two mirror or scanning axes onto the processing line of a further scanner system, wherein, in order to produce a straightened scanning pattern, the rising edges of the scanning curve are in each case masked out.

In FIGS. 5-7, the circles in each case schematically represent the focus midpoints of a pulsed laser beam (processing beam L5) or of a femtosecond laser pulse at the focus Q. The scanning trajectories t illustrated in FIGS. 5, 6, 7, 8a and 8b have laser pulses distributed non-uniformly in specific regions. As a measure against that, depending on the embodiment variant and/or application, the laser beam or the laser pulses are masked out by the filter module 4, for example by means of a shutter or diaphragm 41, as a result of which selectively determined regions of the scanning trajectory t are selected. In the example in FIG. 5, by way of example, optionally the oscillation peaks, which have comparatively more densely successive laser pulses, in the regions R1 are masked out by the filter module 4, preferably by a field stop. In the example in FIG. 6, the rising edges of the scanning trajectory t in the region R2 are in each case masked out, such that selectively only the falling branches of the scanning trajectory t are used for processing, in which case, by way of example, the oscillation peaks are also cut off. Preferably, the region R2 is masked out by a shutter that is arranged at the laser and disposed downstream of the beam source 6 and is closed for masking out the region R2 and is otherwise open. In order to match the pulse separation within a branch or an edge, in a further embodiment variant, by means of the control module 7, the pulse frequency will be adapted depending on the position in the scanning trajectory t (e.g. by means of pulse pickers) or the excursion amplitude A, B of the fast scanner system 5 is altered dynamically. By virtue of the resulting dynamic increase (expansion) or decrease (compression), respectively, in the excursion amplitude F of the scanning movement f, the distance between successive individual femtosecond laser pulses on the scanning curve f or scanning trajectory t can be increased or decreased, respectively, in a simple manner and independently of s and the number of laser pulses within the scanning width E not masked out can thereby be controlled in a variable manner.

Figure 8A:
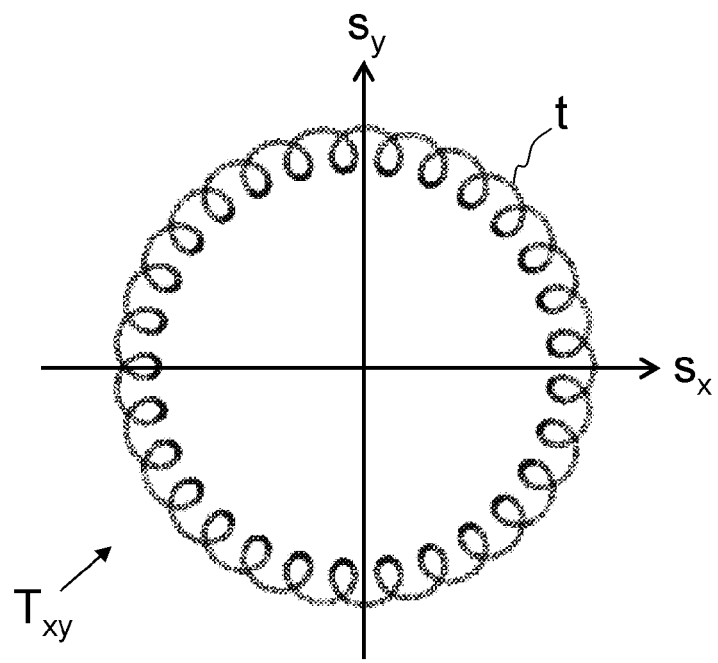
FIG. 8a: illustrates the superimposition of a round scanning curve of one scanner system having two mirror or scanning axes onto a round processing line of a further scanner system.
Figure 8B:
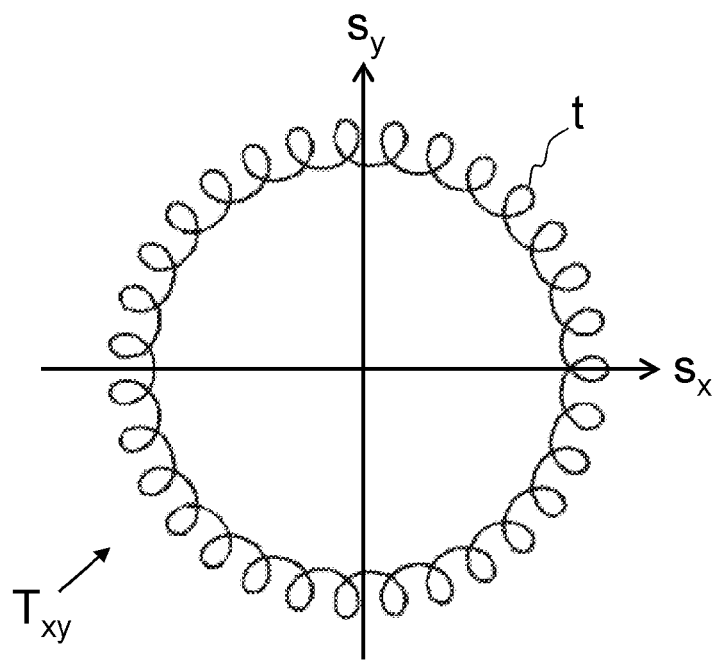

FIGS. 8a and 8b show examples of cycloidal scanning trajectories t produced by the superimposition of round scanning curves f of the fast scanner system 5 onto round processing lines s of the slow scanner system 3. As is illustrated schematically in FIGS. 8a and 8b, the control module 7 or the fast scanner controller is designed to control the fast scanner system 5 in such a way that the laser pulses on the projection plane $P_{xy}$ are deflected onto a round, for example circular or elliptical, scanning curve f, and the control module 7 or the slow scanner controller is designed to control the slow scanner system 3 in such a way that the femtosecond laser pulses L2 deflected by the fast scanner system 5 or the femtosecond laser pulse L3 not masked out by the filter module 4 are deflected or superimposed onto a round processing line s, for example a circular or elliptical processing line s. As can be seen from FIGS. 8a and 8b, the resulting cycloidal scanning trajectories t differ in that the superimposed scanning curves f have an opposite sense of rotation.

A particularly optimum configuration of a cycloidal scanning trajectory t results from the size of the interaction zones, which can be larger than the spot diameter of a laser pulse (cavitation bubbles). Depending on the application, it is entirely expedient if scanning trajectories t are superimposed; by way of example, the loops of the cycloids can fall into the gaps of adjacent cycloids. This latter variant has the advantage that it is simple in terms of control technology because it can be implemented with little or no coupling to the slow scanner system 3.

Finally, it should be mentioned that although the computer program code was assigned to specific functional modules in the description, the person skilled in the art will understand that the computer program code can be changed in a variously structured fashion, without departing from the protected subject matter.

What is claimed is:

1. An ophthalmological device for processing eye tissue using femtosecond laser pulses comprising:
   a projection optical unit for the focused projection of the femtosecond laser pulses into the eye tissue,
   a first beam-deflecting scanner system, disposed upstream of the projection optical unit, configured to scan the eye tissue with the femtosecond laser pulses along a processing line,
   a second beam-deflecting scanner system disposed upstream of the first scanner system, configured to scan the eye tissue with the femtosecond laser pulses on a scanning curve (f) superimposed on the processing line, with a scanning speed that is faster than the scanning speed of the first beam-deflecting scanner system, comprising a first scanning axis and a second scanning axis, the first scanning axis and the second scanning axis being oriented orthogonally with respect to one another, the second scanner system being configured to deflect the femtosecond laser pulses in an oscillating fashion about the first scanning axis and about the second scanning axis, and the first scanner system having a greater degree of excursion in comparison with the second scanner system, and a control module configured to control the deflection of the femtosecond laser pulses about the first scanning axis and the deflection of the femtosecond laser pulses about the second scanning axis in accordance with at least one of defined curve shape, defined curve amplitude and defined curve orientation of the scanning curve (f).

2. The device according to claim 1, wherein the control module is configured to determine the curve orientation of the scanning curve (f) by coupled control of excursion amplitude (B) of the deflection (b) about the first scanning axis and of excursion amplitude (A) of the deflection (a) about the second scanning axis.

3. The device according to claim 1, wherein the control module is configured to determine the curve orientation of the scanning curve (f) by coupled control of excursion amplitude (B) of the deflection (b) about the first scanning axis, of excursion amplitude (A) of the deflection (a) about the second scanning axis, and of the relative phase of the deflection (b) about the first scanning axis and of the deflection (a) about the second scanning axis.

4. The device according to claim 1, wherein the control module is configured to determine the curve amplitude (F) of the scanning curve (f) by coupled control of excursion amplitude (B) of the deflection (b) about the first scanning axis and of excursion amplitude (A) of the deflection (a) about the second scanning axis.

5. The device according to claim 1, wherein the control module is configured to determine the curve shape of the scanning curve (f) by control of the relative phase of the deflection (b) about the first scanning axis and of the deflection (a) about the second scanning axis.

6. The device according to claim 1, wherein the control module is configured to determine the curve shape of the scanning curve (f) by coupled control of the excursion amplitude (B) of the deflection (b) about the first scanning axis and of the excursion amplitude (A) of the deflection (a) about the second scanning axis.

7. The device according to claim 1, wherein the control module is configured to determine the curve shape of the scanning curve (f) by coupled control of the deflection frequency ($\omega_x$) about the first scanning axis and of the deflection frequency ($\omega_y$) about the second scanning axis.

8. The device according to claim 1, wherein the control module is configured to determine a curve shape, definable by Fourier synthesis, of the scanning curve (f) by control of at least one of excursion amplitude (B) of the deflection (b) about the first scanning axis, excursion amplitude (A) of the deflection (a) about the second scanning axis, relative phase of the deflection (b) about the first scanning axis and of the deflection (a) about the second scanning axis, deflection frequency ($\omega_x$) about the first scanning axis, and deflection frequency ($\omega_y$) about the second scanning axis.

9. The device according to claim 1, wherein the control module is configured to control, depending on the processing line at least one of excursion amplitude (B) of the deflection (b) about the first scanning axis, excursion amplitude (A) of the deflection (a) about the second scanning axis, relative phase of the deflection (b) about the first scanning axis and of the deflection a about the second scanning axis, deflection frequency ($\omega_x$) about the first scanning axis, and deflection frequency ($\omega_y$) about the second scanning axis.

10. The device according to claim 1, wherein the control module is configured, in the case of a change in the direction of the processing line ($s_x$, $s_y$), to reduce the excursion amplitude (B) of the deflection (b) about the first scanning axis and to increase the excursion amplitude (A) of the deflection (a) about the second scanning axis.

11. The device according to claim 1, wherein the control module is configured to control the deflection (b) about the first scanning axis and the deflection (a) about the second scanning axis such that the deflection (b) about the second scanning axis is effected with a deflection frequency ($\omega_y$) having a doubled magnitude relative to the deflection (b) about the first scanning axis, and the deflection (a) about the second scanning axis brings about at least partial compensation of the deflection brought about by the first beam-deflecting scanner system in the direction of the processing line ($s_x$).

12. The device according to claim 1, further comprising a diaphragm arranged between the first beam-deflecting scanner system and the second beam-deflecting scanner system and serving for masking out femtosecond laser pulses that are deflected by the second beam-deflecting scanner system into a region (R1) outside a defined scanning width.

13. The device according to claim 1, further comprising a controllable filter module for selectively excluding femtosecond laser pulses in a defined region (R1, R2) of the scanning curve (f).

14. The device according to claim 1, wherein that the control module is configured to control the deflection of the femtosecond laser pulses about the first scanning axis and the deflection of the femtosecond laser pulses about the second scanning axis such that the scanning curve (f) has a round curve shape, and in that the control module is configured to control the scanning speed of the first beam-deflecting scanner system such that a resulting scanning trajectory (t) having a defined trajectory profile arises from the superimposition of the scanning curve (f) onto the processing line.

15. The device according to claim 1, wherein the scanning speed of the second beam-deflecting scanner system is a multiple of the scanning speed of the first beam-deflecting scanner system.

16. The device according to claim 1, wherein the second beam-deflecting scanner system further comprises at least one deflection mirror.

* * * * *